US011453704B2

(12) United States Patent
Chen et al.

(10) Patent No.: US 11,453,704 B2
(45) Date of Patent: Sep. 27, 2022

(54) RECOMBINANT HUMAN REPLICATION-DEFICIENT ADENOVIRUS COMPRISING A MODIFIED NUCLEIC ACID ENCODING THE MARBURG VIRUS ENVELOPE GLYCOPROTEIN

(71) Applicant: Academy of Military Medical Science, PLA, Beijing (CN)

(72) Inventors: Wei Chen, Beijing (CN); Shipo Wu, Beijing (CN); Lihua Hou, Beijing (CN); Yanbo Wen, Beijing (CN); Zhe Zhang, Beijing (CN); Busen Wang, Beijing (CN); Xiaohong Song, Beijing (CN); Jinlong Zhang, Beijing (CN); Ling Fu, Beijing (CN)

(73) Assignee: Academy of Military Medical Science, PLA, Beijing (CN)

( * ) Notice: Subject to any disclaimer, the term of this patent is extended or adjusted under 35 U.S.C. 154(b) by 51 days.

(21) Appl. No.: 16/756,610

(22) PCT Filed: Aug. 27, 2018

(86) PCT No.: PCT/CN2018/102408
§ 371 (c)(1),
(2) Date: Apr. 16, 2020

(87) PCT Pub. No.: WO2019/214110
PCT Pub. Date: Nov. 14, 2019

(65) Prior Publication Data
US 2020/0392188 A1  Dec. 17, 2020

(30) Foreign Application Priority Data
May 7, 2018  (CN) .......................... 201810428286.1

(51) Int. Cl.
*C07K 14/005* (2006.01)
*A61K 39/12* (2006.01)
*C12N 7/00* (2006.01)
*A61K 35/761* (2015.01)
*A61P 31/14* (2006.01)
*A61K 39/00* (2006.01)

(52) U.S. Cl.
CPC .......... *C07K 14/005* (2013.01); *A61K 35/761* (2013.01); *A61K 39/12* (2013.01); *C12N 7/00* (2013.01); *A61K 2039/57* (2013.01); *A61K 2039/575* (2013.01); *A61P 31/14* (2018.01); *C07K 2319/02* (2013.01); *C12N 2710/10021* (2013.01); *C12N 2710/10043* (2013.01); *C12N 2710/10051* (2013.01); *C12N 2710/10341* (2013.01); *C12N 2760/14221* (2013.01); *C12N 2760/14222* (2013.01); *C12N 2760/14234* (2013.01)

(58) Field of Classification Search
CPC ................. A61K 35/761; A61K 39/12; C12N 2760/14221; C12N 2710/10341; C12N 2760/14234; C12N 15/86; C07K 2319/02; C07K 14/005
See application file for complete search history.

(56) References Cited

U.S. PATENT DOCUMENTS 10,172,932 B2 * 1/2019 Chen ...................... C12N 15/86

FOREIGN PATENT DOCUMENTS

| CN | 106868025 A | 6/2017 |
| CN | 107022007 A | 8/2017 |
| WO | 2016138312 A2 | 9/2016 |

OTHER PUBLICATIONS

Gao, W., et al., 2004, UpGene: Application of a web-based DNA codon optimization algorithm, Biotechnol. Prog. 20:443-448.*
Towner, J. S., et al., Jul. 2006, Marburgvirus genomics and association with a large hemorrhagic fever outbreak in Angola, J. Virol. 80(13):6497-6516.*
Golden, A., et al., 1998, Effect of promoters and signal sequences on the production of secreted HIV-1 gp120 protein in the baculovirus system, Prot. Exp. Purif. 14:8-12.*
Wang, D., et al., 2006, De novo synthesis of Marburg virus antigens from adenovirus vectors induce potent humoral and cellular immune responses, Vaccine 24:2975-2986.*
Towner, J. S., et al., Jul. 2006, Marburg Genomics and Association with a Large Hemorrhagic Fever Outbreak in Angola, J. Virol. 80(13):6497-6516.*
GenBank DQ447660.1, Jun. 2006, Lake Victoria Marburgvirus—Angola 2005 strain Ang0998, complete genome, pp. 1-7.*
GenBank: KY425629.1—Marburg marburgvirus isolate IRF0169, partial genome (6 pages).

* cited by examiner

Primary Examiner — Jeffrey S Parkin
(74) Attorney, Agent, or Firm — Fox Rothschild LLP

(57) ABSTRACT

The present invention relates to a nucleotide sequence as shown in SEQ ID NO: 1 for encoding a Marburg virus envelope glycoprotein, and to a human replication-deficient recombinant adenovirus capable of expressing the nucleotide sequence and a preparation method therefor, as well as an application thereof in the preparation of a vaccine against Marburg virus disease. The vaccine uses an E1 and E3 deleted replication-deficient human type-5 adenovirus as a vector, and HEK293 cells integrating an adenovirus E1 gene as a packaging cell line, and a protective antigen gene carried is a codon-optimized Marburg virus Angola strain envelope glycoprotein gene. After codon optimization of the envelope glycoprotein gene, significant expression of envelope glycoprotein can be detected in transfected cells.

11 Claims, 17 Drawing Sheets

Specification includes a Sequence Listing.

RECOMBINANT HUMAN REPLICATION-DEFICIENT ADENOVIRUS COMPRISING A MODIFIED NUCLEIC ACID ENCODING THE MARBURG VIRUS ENVELOPE GLYCOPROTEIN

TECHNICAL FIELD

The present invention relates to an isolated nucleic acid molecule, to be specific, to an isolated nucleic acid molecule encoding a virus envelope glycoprotein, belonging to the field of genetic engineering technology.

BACKGROUND OF THE INVENTION

Marburg virus (MARV) is a kind of hemorrhagic fever virus, which is a member of Filoviridae family MARV can cause Marburg virus disease, a viral hemorrhagic fever in humans and non-human primates, with a mortality rate of up to 90%. MARV is an exceptionally dangerous pathogen, which is classified as biosafety level-4 pathogen by WHO (requires to conduct related operations in biosafety level 4 laboratory), as category A priority pathogen by National Institutes of Health and National Institute of Allergy and Infectious Diseases, and as category A bioterrorism agent by Centers for Disease Control and Prevention, USA.

Marburg virus is named after Marburg, Germany, which was initially detected in 1967 after small-scale outbreaks in Marburg and Frankfurt in Germany, and in Belgrade in Yugoslavia, when laboratory workers were exposed to tissues of MARV-infected African green monkeys imported from Uganda, resulting in 31 cases of infection and 7 deaths.

Marburg virus is mainly endemic in sub-Saharan Africa, with fruit bats as the potential hosts. In human, MARV spreads through contaminated body fluids exposure via sexual intercourse and contact with damaged skin, and the funeral rituals in Africa is a major risk of virus transmission. Two large outbreaks of MARV occurred in Congo between 1998 to 2000, leading to 154 cases of infection and 128 deaths, with a mortality rate of 83%; and in Angola between 2004 to 2005, leading to 252 cases of infection and 227 deaths, with a fatality rate of 90%.

Marburg virus strains consist of Ravn virus and Marburg virus, and the latter can be further divided into strain A and strain B. Strain A is isolated from Uganda (5 strains in 1967), Kenya (1980) and Angola (2004-2005); and strain B is isolated from the Republic of the Congo (1999-2000) and Uganda (2007-2009). The gene homology of Ravn virus and Marburg virus is approximate 80%, and that of strain A and strain B is greater than 90%.

Marburg virus glycoprotein (MARV-GP) is the unique surface protein of Marburg virus envelope. MARV-GP plays a key role in the pathogenesis of Marburg virus, which is also the main target protein that induces the body to produce a protective immune response. MARV-GP is basically used as the target antigen for Marburg virus vaccines under development currently, including DNA vaccines, subunit vaccines, non-replicating and replicating virus-vectored vaccines. Several vaccines have achieved good immune protective effect in animal models, and some have entered clinical trials, including DNA vaccines and modified vaccinia virus Ankara (MVA)-vectored Ebola-Marburg combined vaccine, and chimpanzee adenovirus type 3 (ChAd3)-vectored Marburg vaccine. However, as of April 2018, there is no approved Marburg vaccine in the world.

AdMax system consists of LoxP site-containing shuttle plasmid, backbone plasmid, and HEK293 cell line. Recombinant adenovirus is generated by genetic recombination of exogenous gene sequence with the backbone plasmid in HEK293 cells after the DNA fragment is inserted into the shuttle plasmid. The recombinant adenovirus packaged by AdMax system is a E1 and E3 deleted replication-deficient adenovirus. And the vaccine based on this has the advantage of high safety. Furthermore, AdMax system also has other advantages, such as efficient, stable, convenient and fast packaging and high yield. Previously, the inventors of the present application used AdMax system to successfully prepare a recombinant Ebola virus disease vaccine with Zaire-type Ebola virus Makona strain envelope glycoprotein as the target antigen, which is an example of the rapid development of the vaccine, from gene synthesis to clinical trials within five months, highlighting the advantages of the Admax system.

The expression level of target protein is an essential factor for the immune response of the live virus-vectored vaccine. High-level expression of target protein can achieve good immune response with reduced immune dose, leading to the decrease in the live virus vector-related adverse reactions of vaccines. Therefore, the immune response of the vaccine can be enhanced by higher expression and secretion to outside of the cell of envelope glycoprotein via codon optimization of MARV-GP gene and change of the signal peptide.

SUMMARY OF THE INVENTION

Technical Problem

In 2014, the largest Ebola outbreak occurred in West Africa, causing more than 28,000 cases of infection and over 11,000 deaths. Ebola virus and Marburg virus are members of Filoviridae family, and as the most dangerous viruses, both can cause large-scale epidemics, which may be used as biological weapons for biological warfare or biological terror. Therefore, the development of a safe and effective Marburg virus vaccine is crucial. Based on the real threat of Marburg virus and the successful experience of preparation of a recombinant Ebola virus disease vaccine by using AdMax system, the applicant intends to achieve high-level expression of envelope glycoprotein in eukaryotic cells through codon optimization of MARV-GP, and to provide a recombinant adenovirus-vectored Marburg virus disease vaccine with the capacity of inducing higher levels of humoral and cellular immune responses at the same dose level.

Solutions to Technical Problem

For the above purposes, the present invention first provides an isolated nucleic acid molecule as shown in SEQ ID NO: 1 for codon optimization of MARV-GP gene of Marburg virus disease vaccine. The recombinant adenovirus-vectored Marburg virus disease vaccine is obtained after being packaged with an E1 and E3 deleted replication-deficient human type-5 adenovirus as a vector, and HEK293 cells integrating an adenovirus E1 gene as a packaging cell line.

The present invention also provides a vector containing the above isolated nucleic acid molecule.

In a preferred embodiment, the vector is pDC316.

The present invention also provides a human replication-deficient recombinant adenovirus capable of expressing the above isolated nucleic acid molecule.

In a preferred embodiment, the recombinant adenovirus vector is derived from the AdMax adenovirus system.

The present invention also provides a use of the above-mentioned recombinant adenovirus vector in preparation of the vaccine for Marburg virus disease prevention.

In a preferred embodiment, the recombinant adenovirus is prepared as an injection powder in the above application.

Finally, the present invention provides a method for preparing the above-mentioned recombinant adenovirus capable of expressing MARV-GP. The method includes the following steps:

(1) Construction of a shuttle plasmid vector containing an isolated nucleic acid molecule encoding a MARV-GP;

(2) Transfection of the vector of step (1) into host cell together with backbone plasmid;

(3) Cultivation of the host cells of step (2);

(4) Extraction of human replication-deficient recombinant adenoviruses capable of expressing MARV-GP from the host cells of step (3).

Preferably, the vector of step (1) is pDC316.

Preferably, the backbone plasmid of step (2) is pBHGlox$^\Delta$E1, 3Cre. Both plasmids belong to the AdMax adenovirus system, and are used together in host cell for packaging of recombinant adenovirus containing the nucleotide sequence encoding MARV-GP.

Preferably, the cells of step (3) are HEK293 cells.

Preferably, two-step column chromatography with Source 30 Q and Sepharose 4 FF is used in step (4) for purification of Marburg virus disease vaccine.

Beneficial Effects of the Present Invention

After animals are immunized with the recombinant adenovirus capable of expressing MARV-GP provided by the present invention, which is used as the Marburg virus disease vaccine, strong cellular and humoral immune response are induced in a short time. Challenged with the mouse adapted strain of Marburg virus 4 weeks post immunization by the vaccine, all immunized mice survive, while all control mice die within 6 to 8 days after challenged, indicating efficacious protection of the vaccine against Marburg virus. The preparation of the vaccine is simple, which can be produced scale-up in a short period in response to emergent Marburg outbreaks and bioterrorism attacks. Moreover, the expression of MARV-GP can only be detected in transfected cells by the codon optimized gene encoding the vaccine target protein, and the humoral and cellular immune responses induced by the recombinant adenovirus-vectored vaccine packaged on the basis of this codon optimized gene for Marburg virus disease are significantly improved. The improvement of immune level is of great significance to the prevention against Marburg virus infection

BRIEF DESCRIPTION OF THE DRAWINGS

FIG. 2 is a graph of the identification of in vitro expression of MARV-GP.

FIG. 7 is a graph of the identification of MARV-GP expression of samples of purified Marburg virus disease vaccine candidate strains.

DETAILED DESCRIPTION OF THE INVENTION

Examples

The present invention is further described with specific examples below, and the advantages and features of the present invention will become clearer with the description. However, these examples are only exemplary, and do not constitute any limitation on the protection scope defined by the claims of the present invention.

Example 1. Preparation of Human Replication-Deficient Adenovirus-Vectored Marburg Virus Disease Vaccine 1. Optimization and Synthesis of MARV-GP Gene The envelope glycoprotein of the Marburg virus strain ang0998 (Genebank ID: DQ447660.1) was selected as the target antigen of the Marburg virus vaccine, which was endemic in Angola, Africa, between 2004 and 2005.

Upgene software (Gao, W. Rzewski, A. Sun, H. Robbins, P. D. &Gambotto, A. UpGene: Application of a web-based DNA codon optimization algorithm. Biotechnol Prag, 2004. 20(2): p. 443-8.) was used for optimizing the codon of the gene. The rare codons was changed by the optimal codons in host cells, meanwhile, the stability of post-transcription mRNA was strengthened, which made it more suitably expressed in eucaryotic host cell.

After gene optimization, The variation of the MARV-GP gene sequence from the original GP gene sequence was 26.1%. Meanwhile, the original signal peptide (1aa-18aa) was replaced by the signal peptide of Tissue Plasminogen Activator (tPA), then Kozak sequence was added in front of the translation initiation codon, with restriction enzyme sites HindIII and SaII as the upstream and downstream restriction site, respectively. The MARV-GP gene was synthesized for recombinant plasmid construction after gene optimized and signal peptide replaced. Besides, the original sequence of the MARV-GP gene was also synthesized as a control. See SEQ ID NO:1 for the optimized MARV-GP gene sequence (with HindIII and SaII as the restriction sites), and see SEQ ID NO:2 for the original MARV-GP gene sequence (with HindIII and SaII as the restriction sites).

Figure 1:
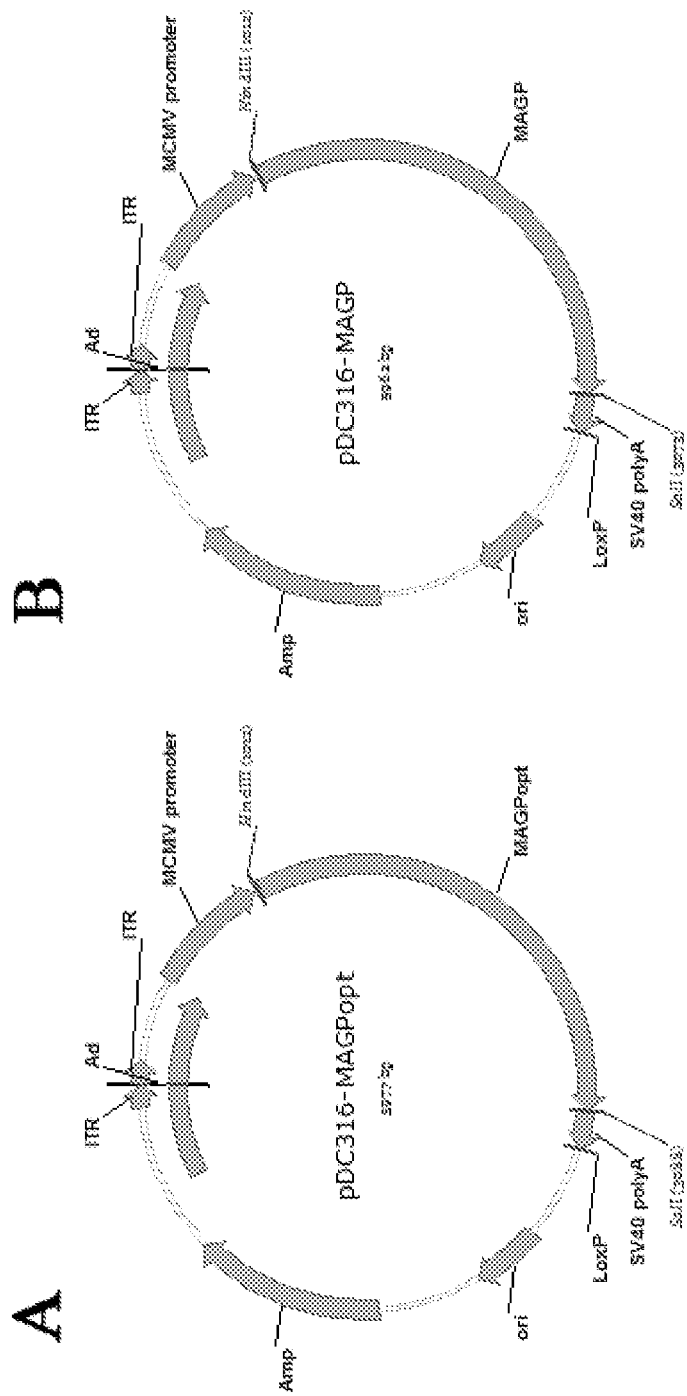
FIG. 1 provides the map of the shuttle plasmid.

2. Construction of Vectors and Identification of In Vitro Expression of MARV-GP 2.1 Construction of Vectors The above synthesized gene sequence is double-digested with HindIII and SalI, and the target gene fragment is recovered and connected to the shuttle plasmid pDC316 of the AdMax adenovirus system (Microbix Biosystems Inc., Canada), and then is transformed into DH5-α competent cells and coated on $Amp^r$ LB plate. Monoclones are selected for colony PCR identification, and sequenced. Plasmid of MARV-GP gene sequence without codon optimization is marked as pDC316-MAGP, whereas plasmid of MARV-GP gene with codon optimization is marked as pDC316-MAGPopt. The plasmid map is shown in FIG. 1, wherein A indicates the plasmid map of pDC316-MAGPopt, and B represents the plasmid map of pDC316-MAGP.

2.2 Identification of In Vitro Expression of MARV-GP

Each of the two shuttle plasmids constructed above and pDC316 vector are transfected into HEK293 cells by using TurboFect Transfection Reagent (Thermo Scientific, #R0531), and the cells are collected at 48 hours post transfection for Western blot detection. The experimental method is as follows:

Transfection: One day before the experiment, HEK293 cells are inoculated into a 6-well plate with $8 \times 10^5$ cells/well and cultured overnight at 37° C. in 5% $CO_2$ incubator. 1 hour prior to transfection, the medium is changed to fresh MEM medium containing 2% FBS, with 2 mL per well. During transfection, 2 μg of corresponding plasmid is taken for each transfection well, added to 200 μL of FBS-free MEM medium, and mixed. 3 μL of transfection reagent is added and mixed gently. The mixture is incubated at room temperature for 15 min. The mixture of plasmid and transfection reagent is gently dripped into the 6-well plate and mixed gently. Cells are cultured at 37° C. in 5% $CO_2$ incubator. 5 hours later, the medium is changed to a fresh MEM medium with 10% FBS. Cells are collected at 48 hours post transfection to prepare samples for Western blot detection.

Sample preparation: 48 hours post transfection, the medium is carefully aspirated and discarded, and cells are washed once with PBS. The 6-well plate is placed on ice, and 120 μL of cell lysis buffer (1×SDS-PAGE buffer containing 50 mmol/L DTT, 1× protease inhibitor, and 250 U/mL nuclease) is added to each well. Lysed cells are collected by a cell scraper, and transferred to a 1.5 mL EP tube and placed into an ice bath for 15 min. Cells are heated at 95° C. for 5 min, then cooled in an ice bath, and centrifuged at 12000 rpm for 5 minutes at 4° C. The supernatant is collected, dispensed and stored frozen for Western blot detection.

Western blot detection: 10-well 12% SDS-PAGE gel is used for SDS-PAGE, and the samples are loaded with 10 μL per well. Electrophoresis conditions: 80 V, 15 min; 180 V, until bromophenol blue migrates out of the gel. The protein on the SDS-PAGE gel is transferred to nitrocellulose membrane by an electric transfer apparatus at 300 mA for 1 h. After electroporation, the nitrocellulose membrane is blocked with 5% skim milk for 1 h, and then anti-MARV-GP rabbit polyclonal antibody (Abcam, ab190459) is added at dilution of 1:2000. The mixture is left at 4° C. overnight. The membrane is washed 4 times with Western blot wash buffer and shaken on the shaker for 7 minutes each time. Then HRP-labeled goat anti-rabbit IgG antibody (CST, 7074S) diluted 1:5000 in 5% skim milk is added, and the mixture is incubated for 1 hour at room temperature. The membrane is washed times with Western blot wash buffer. Immobilon™ Western Chemiluminescent HRP Subsrate (MILLIPORE, Cat. No. WBKLS0500) is used for chemiluminescence reaction, and chemiluminescence imager is used to capture images at different exposure times.

Figure 2:
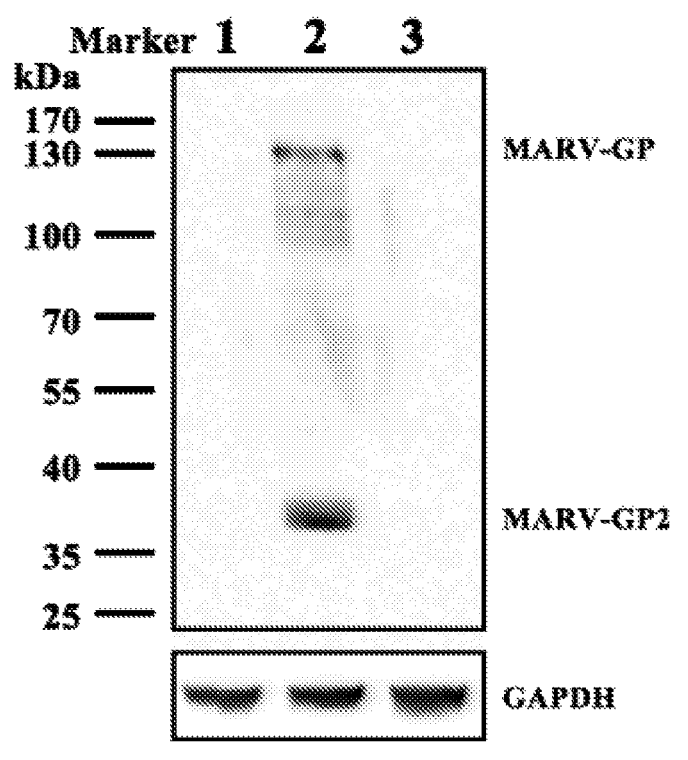

GAPDH is used as the loading control, and results are shown in FIG. 2, wherein lane 1 indicates the cells transfection of pDC316 vector; lane 2 depicts the cells transfection of codon-optimized shuttle plasmid pDC316-MAGPopt; and lane 3 represents cells transfection of non-codon-optimized shuttle plasmid pDC316-MAGP. The results suggest that expression of MARV-GP can only be detected in transfected HEK293 cells with the codon-optimized shuttle plasmid pDC316-MAGPopt.

3. Packaging, Preparation and Identification of the Vaccine 3.1 Packaging of the Vaccine The above constructed vectors pDC316-MAGP and pDC316-MAGPopt are respectively co-transfected into HEK293 cells with the backbone plasmid pBHGlox$^\Delta$E1, 3 Cre of the AdMax adenovirus system, in order to package the recombinant adenovirus. The process is as follows:

a) On the day before transfection, HEK293 cells are inoculated into a 6-well plate with $5 \times 10^5$ cells/well, with MEM+10% FBS as the medium, and are cultured overnight at 37° C. in 5% $CO_2$ incubator.

b) On the day of transfection, cells continue to be cultured in fresh MEM medium with 10% FBS. When cells grow to cover 80%-90% of the well bottom, the backbone plasmid (pBHGlox$^\Delta$E1, 3 Cre) and shuttle plasmid are co-transfected to HEK293 cells with Lipofectamine™ 2000 liposomes according to the instruction of the reagent. The specific steps are as follows:

(1) 4 μg of backbone plasmid and 1 μg of shuttle plasmid are taken for each transfection well, and mixed.

(2) The plasmids are diluted with 300 μL of serum-free MEM medium and left at room temperature for 5 min.

(3) 10 μL of liposomes are taken and diluted with 300 μL of serum-free MEM medium, left at room temperature for 5 min.

(4) The plasmids of step (2) and liposomes in step (3) are mixed, and left at room temperature for 30 minutes in the dark. Then the mixture is added to the cells.

c) On the next day after transfection, the cells which cover the whole bottom of the well are passaged into a 25 $cm^2$ cell culture flask, and continue to be cultured in MEM medium containing 5% FBS. Daily observation is conducted, and cells are passaged into a 75 $cm^2$ cell culture flask when they cover the bottom of the flask. Daily observation for the cells is performed. The recombinant virus generates when the cells become large and round, in shape of grape, and obvious plaques begin to appear. Virus are collected when cell lesion appears and the cells are detached from the bottom.

The cell culture flasks with new virus are frozen in a refrigerator at −70° C. and thawed in a water bath at 37° C. for three times, to let virus fully release from the cells. The frozen-thawed solution is centrifuged at 3000 rpm for 5 min, and the supernatant containing virus is collected. The supernatant is the primary virus strain (P1), and used for subsequent amplification of a large number of viruses.

The primary virus strains of the recombinant adenovirus with different MARV-GP gene are recorded as Ad5-MAGP and Ad5-MAGPopt, respectively.

3.2 Identification of the Primary Virus Strain

3.2.1 PCR Amplification of MARV-GP Gene and Sequencing

The following universal primers of pDC316 vector are used to amplify the sequence of MARV-GP:

```
pDC316-F:
ACGTGGGTATAAGAGGCG,
and pDC316-R:
CGATGCTAGACGATCCAG.
```

Primary virus strain genomes of Ad5-MAGP and Ad5-MAGPopt are extracted according to the instruction of viral genomic DNA/RNA extraction kit (DP315, Tiangen Biotech), and identified by PCR with the above primers.

PCR amplification conditions are:

TABLE 1

| | |
|---|---|
| Genomic DNA of samples for test | 1 μL |
| Upstream primer | 0.4 μL |
| Downstream primer | 0.4 μL |
| dNTP | 1.6 μL |
| LA Taq DNA Polymerase | 0.2 μL |
| 10 × LA Buffer | 2 μL |
| ddH2O | 14.4 μL |

Reaction Procedure:

| | | |
|---|---|---|
| 94° C., 5 min. | | |
| 94° C. | 30 s | |
| 56° C. | 30 s | 30 cycles |
| 72° C. | 120 s | |
| 72° C., 10 min. | | |

Figure 3:
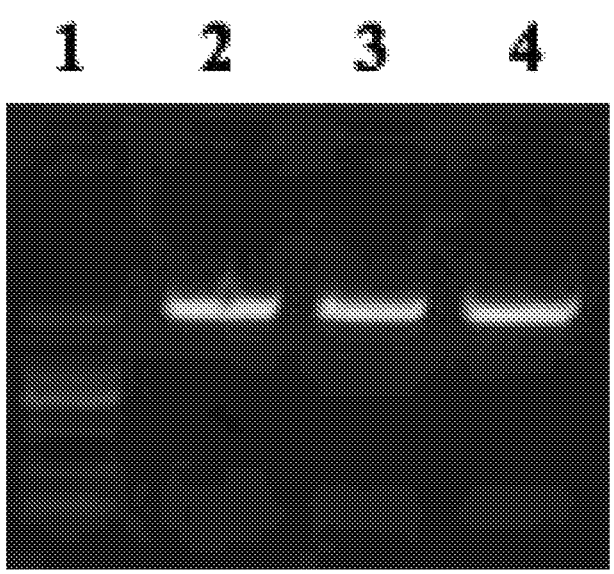
FIG. 3 depicts PCR identification of primary virus strain.

The results of PCR amplification are shown in FIG. 3, where lane 1 indicates DNA ladder (Takara, DL2000); lane 2 shows DNA/RNA amplification products of Ad5-MAGP primary virus strain; lane 3 depicts DNA/RNA amplification products of Ad5-MAGPopt primary virus strain; and 4 represents the amplification products of plasmid pDC316-MAGPopt (positive control). Results suggest correct band size after amplification. Target bands 2 and 3 are gel-recovered and sequenced. The alignment results indicate that the sequences tested are completely correct.

3.2.2 Identification of MARV-GP Expression of Marburg Virus Disease Vaccine Candidate Strain.

Figure 4:
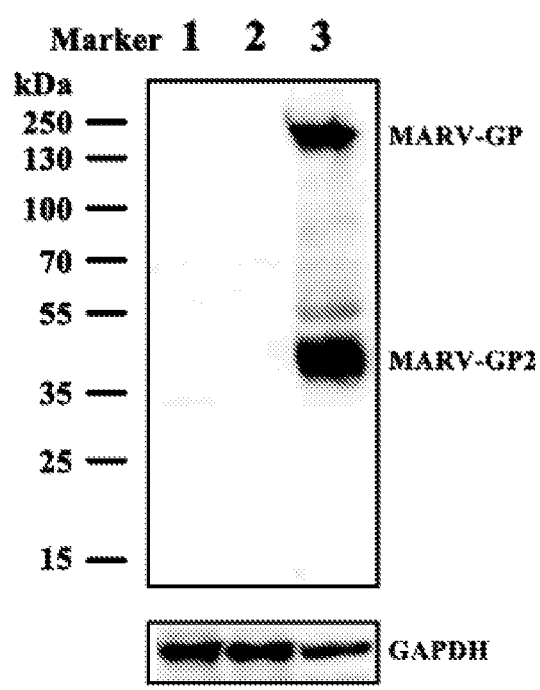
FIG. 4 is the identification of MARV-GP expression of the primary virus strain of Marburg virus disease vaccine.

HEK293 cells are infected with Ad5-MAGP and Ad5-MAGPopt, and collected 48 hours later for Western blot detection of MARV-GP. No MARV-GP is detected for Ad5-MAGP infection. However MARV-GP is detected for Ad5-MAGPopt infection, as shown in FIG. 4, wherein lane 1 indicates blank cells; lane 2 depicts Ad5-MAGP infected cells; and lane 3 represents Ad5-MAGPopt infected cells.

3.3 Expanded Culture and Purification of Ad5-MAGPopt and Ad5-MAGP

3.3.1 Small-Scale Culture of Ad5-MAGPopt and Ad5-MAGP

HEK293 cells are suspension-cultured at 37° C. in 5% $CO_2$, at 130 rpm. When infected with the virus strain, cells with a viability greater than 95% are diluted to $1.0 \times 10^6$ cells/mL, with 1 L as the final volume. HEK293 cells are infected with recombinant adenovirus at MOI 10, and are cultured at 37° C. in 5% $CO_2$, with shaken at 130 rpm. Samples are collected every 24 hours for the measurement of cell viability and density. About 72 hours post inoculation, when the cell viability drops to below 40%, 10 mL tween-20 (final concentration, 1%) is added into the flasks and the flasks continue to be shaken for 1 hour at 130 rpm. The cell culture harvest is centrifuged at 6000 rpm for 30 min, and the supernatant is taken and stored frozen at −70° C. The precipitate is resuspended in an equal volume of 20 mM Tris, 250 mM NaCl, 1 mM $MgCl_2$, 1% tween-20, pH 7.5, and the mixture is shaken at 37° C., 130 rpm for 1 h. The suspension is centrifuged at 6000 rpm for 45 min, then stored frozen at −70° C.

3.3.2 Purification of Ad5-MAGPopt and Ad5-MAGP

The above recombinant adenovirus culture harvest stored frozen at −70° C. are thawed for purification. The harvest is ultrafiltrated and concentrated to 500 mL with 300 kDa membrane, and added with an equal volume of 20 mM Tris+150 mM NaCl+2 mM $MgCl_2$ pH7.5 (solution A). Finally 300 mL viral solution is got after 3 times of ultrafiltration. Benzonase (30 U/mL) is added, and the mixture is left in a water bath at 37° C. for 4 h.

Figure 5:
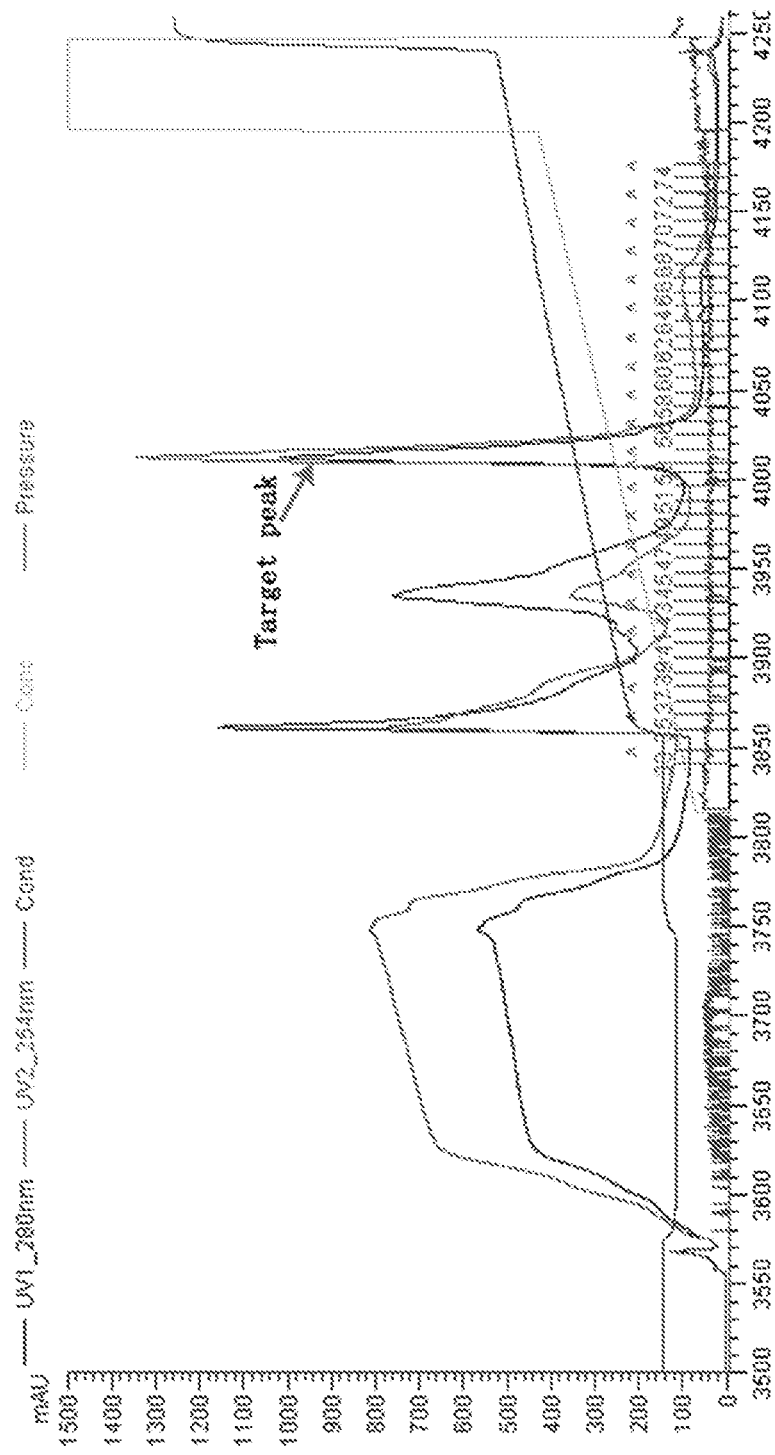
FIG. 5 shows chromatography process of Source 30Q.

Two-step column chromatography with Source 30Q and Sepharose 4 FF are used to purify adenovirus particles. The column chromatography in the first step is to remove most of the miscellaneous protein and to collect the eluted peaks, whereas the column chromatography in the second step is to remove the miscellaneous DNA residue and some miscellaneous protein, and the samples collected are flow-through samples. The specific process is as follows:

Chromatography with Source 30Q: The column is equilibrated with solution A, and samples are loaded at a flow rate of 5 mL/min. After sample loading, solution A is used to equilibrate the column at 10 mL/min for 50 min. 0%-30% solution B is used for gradient elution, and the elution peaks are harvested in separate tubes. Finally, 100% solution B is used for elution. Solution B is 20 mM Tris+2 M NaCl+2 mM $MgCl_2$ pH7.5. Elution peaks are shown in FIG. 5.

Chromatography with Sepharose 4 FF: The above elution peaks are further purified with Sepharose 4 FF. The mobile phase is solution A, the flow rate is 5 mL/min, the pressure limit is 0.3 MPa, and the flow-through are harvested. Purified adenoviral particles are filtration-sterilized through a 0.22-μm filter and stored in a refrigerator at −70° C.

3.4 Identification and Titer Determination of Ad5-MAGPopt and Ad5-MAGP

3.4.1 PCR Amplification of MARV-GP Sequence and Sequencing

Figure 6:
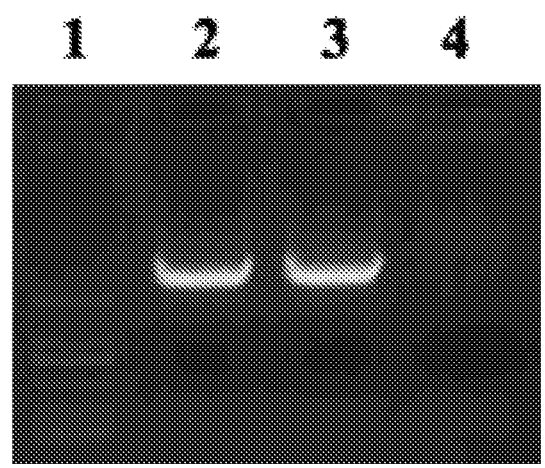
FIG. 6 provides PCR identification of samples of purified Marburg virus disease vaccine.

The method and process are the same as those described in section 3.2.1, and results are shown in FIG. 6, wherein lane 1 indicates DNA ladder (Takara, DL2000); lane 2 shows DNA/RNA amplification products of purified Ad5-MAGP; lane 3 depicts DNA/RNA amplification products of purified Ad5-MAGPopt; and lane 4 represents negative control. Results suggest that target sequence are detected in the purified Ad5-MAGPopt and Ad5-MAGP. Sequencing results show the DNA sequences from Ad5-MAGPopt and Ad5-MAGP are totally correct.

3.4.2 Western Blot Detection

Figure 7:
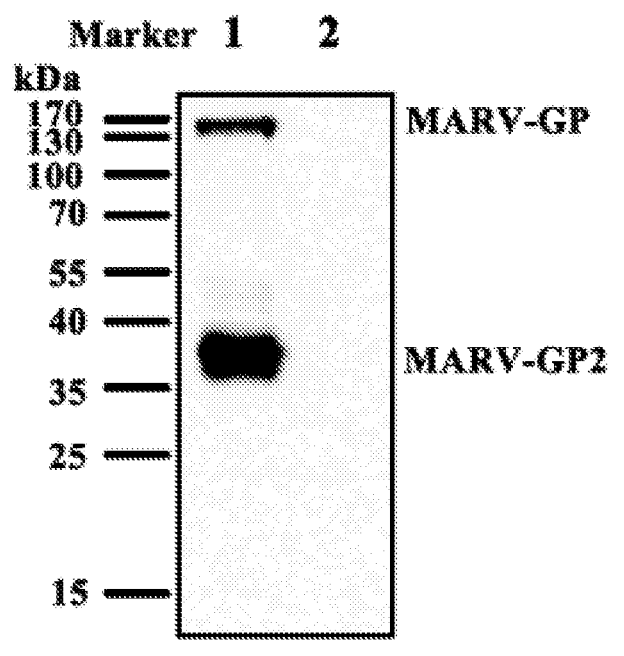

HEK293 cells are infected with Ad5-MAGPopt and Ad5-MAGP at MOI 10, and cells are collected 48 hours post infection for Western blot detection of MARV-GP. Results are shown in FIG. 7, wherein lane 1 indicates Ad5-MAGPopt infected cells; and lane 2 indicates Ad5-MAGP infected cells. MARV-GP can be detected only in Ad5-MAGPopt-infected cells, not in Ad5-MAGP-infected cells.

3.4.3 Titer Determination

Clontech Adeno-X™ Rapid Titer Kit is used to measure the titer of the purified Ad5-MAGPopt and Ad5-MAGP. The procedure is conducted according to the instructions of the kit, and the specific method is as follows:

a) HEK293 cells are seeded into a 24-well plate with $5\times10^5$ cells/mL, 0.5 mL per well, with MEM+10% FBS as the medium.

b) The adenovirus to be detected are diluted 10-fold with medium, from $10^{-2}$ to $10^{-6}$, to prepare a series of diluted virus samples, and 50 μL per well is added to the cells.

c) Cells are cultured at 37° C. in 5% $CO_2$ incubator for 48 hours.

d) Cell medium is aspirated and discarded to allow cells to dry slightly (do not over-dry). 0.5 mL of ice-cold methanol is gently added to each well, and the plate is left at −20° C. for 10 minutes to fix the cells.

e) Methanol is aspirated and discarded, and cells are gently washed 3 times with PBS+1% BSA. 0.25 mL of Anti-Hexon antibody diluent (1:1000 dilution) is added to each well, and incubate at 37° C. for 1 hour.

f) Anti-Hexon antibody is aspirated and discarded, and cells are gently washed 3 times with PBS+1% BSA. 0.25 mL of HRP-labeled rat anti-mouse antibody (1:500 dilution) is added to each well, and incubate at 37° C. for 1 h.

g) Prior to removing the Rat Anti-Mouse Antibody (HRP conjugate), prepare DAB working solution by diluting 10×DAB Substrate 1:10 with 1× Stable Peroxidase Buffer. Allow the 1×DAB working solution to come to room temperature.

h) The rat anti-mouse antibody is aspirated and discarded, and cells are gently washed 3 times with PBS+1% BSA. 0.25 mL of DAB working solution is added to each well, and incubate at room temperature for 10 min.

i) DAB working solution is aspirated and discarded, and cells are gently washed 2 times with PBS.

j) Brown/black positive cells are counted under a microscope. At least 3 fields are randomly counted for each well, and the mean number of positive cells is calculated.

h) Infection titer (ifu/mL) is calculated, with the following formula:

$$\text{Infection titer } (\mathit{ifu}/\text{mL}) = \frac{(\text{infected cells/field}) \times (\text{fields/well})}{\text{volume virus (mL)} \times (\text{dilution factor})}$$

Results of titer determination show that the infection titer of the elution peak of Sepharose 4 FF chromatography can reach $1.0\times10^{10}$ ifu/mL or above.

Example 2. Immunological Evaluation of Ad5-MAGPopt and Ad5-MAGP in a Mouse Model 1. Materials
1.1. Animals
SPF female BALB/c mice (age 4-6 weeks) are used, which are purchased from Beijing Weitong Lihua Experimental Animal Technology Co., Ltd and raised in the animal center of Academy of Military Medical Science.

1.2. Reagent
Fluorescently labeled antibodies FITC anti-mouse CD8a (Clone 5H10-1), PE anti-mouse IFNγ (Clone XMG1.2), PerCP/Cy5.5 anti-mouse CD3 (Clone 17A2), Alexa Fluor® 700 anti-mouse CD4 (Clone RM4-5), APC/Cy7 anti-mouse CD14 (Clone Sa14-2), APC/Cy7 anti-mouse CD19 (Clone 6D5), Brilliant Violet 421™ anti-mouse CD107a (Clone 1D4B), Brilliant Violet 510™ anti-mouse CD154 (Clone MR1), Brilliant Violet 605™ anti-mouse IL-2 (Clone JES6-5H4) and erythrocyte lysis buffer are purchased from Biolegend. Fluorescently labeled antibodies PE/Cy7 anti-mouse TNF (Clone MP6-XT22), Mouse BD Fc Block™, BD Perm/Wash™ Buffer, BD Cytofix/Cytoperm™ Fixation and Permeabillization Solution, BD GolgiStop™, BD GolgiPlug™, BD™ ELISPOT mouse IFNγ Set, BD™ ELISPOT AEC substrate set and flow tubes are purchased from BD. LIVE/DEAD™ Fixable Near-IR Dead Cell Stain Kit is purchased from Invitrogen, BSA is purchased from Merck, HRP-labeled goat anti-mouse IgG antibody is purchased from Abcam, TMB single-component substrate solution is purchased from Solarbio, 24-well plates and ELISA plates are purchased from Corning, Marburg GP overlapping peptide library and CTL epitope LI-9 are synthesized by Shanghai Gill Biochemical Company, DMSO, PMA and ionomycin are purchased from Sigma, fetal bovine serum (PBS) and RPMI1640 mediums are purchased from Gibco, truncated Marburg virus GP is expressed and purified by our laboratory, 2N sulfuric acid, 70% alcohol and PBS are self-prepared.

2 Immunization of Mice
Based on the experimental design, the Marburg candidate vaccines and the control vaccines are diluted with physiological saline to specific concentrations, and mice are immunized by 1 mL syringes via injection to medial muscle of the left posterior thigh, with 50 μL per mouse. The immune dose for each mouse is $1\times10^8$ ifu, $1\times10^7$ ifu, $1\times10^6$ ifu or $1\times10^5$ ifu, and groups of mice are shown in Table 1, Table 2 and Table 3.

TABLE 1

Groups of mice for evaluating humoral immune response

| Name of vaccine | Dose | Route of immunization | Number of mice in the group |
| --- | --- | --- | --- |
| Ad5-MAGPopt | $10^8$ ifu | Intramuscularly | 12 |
| Ad5-MAGPopt | $10^7$ ifu | Intramuscularly | 12 |
| Ad5-MAGPopt | $10^6$ ifu | Intramuscularly | 12 |
| Ad5-MAGP | $10^8$ ifu | Intramuscularly | 12 |

TABLE 2

Groups of mice for evaluating cellular immune response

| Name of vaccine | Dose | Route of immunization | Number of mice in the group |
| --- | --- | --- | --- |
| Ad5-MAGPopt | $10^8$ ifu | Intramuscularly | 12 |
| Ad5-MAGP | $10^8$ ifu | Intramuscularly | 12 |
| Ad5-Luc | $10^8$ ifu | Intramuscularly | 12 |

TABLE 3

Groups of mice for evaluatinge cellular immune response at different doses

| Name of vaccine | Dose | Route of immunization | Number of mice in the group |
| --- | --- | --- | --- |
| Ad5-MAGPopt | $10^8$ ifu | Intramuscularly | 6 |
| Ad5-MAGPopt | $10^7$ ifu | Intramuscularly | 6 |
| Ad5-MAGPopt | $10^6$ ifu | Intramuscularly | 6 |
| Ad5-MAGPopt | $10^5$ ifu | Intramuscularly | 6 |
| Ad5-Luc | $10^8$ ifu | Intramuscularly | 6 |

3. Humoral Immune Response
3.1. Blood Collection and Serum Separation
Blood is collected from the immunized mice tail vein at specific time points and left at room temperature for over 1 h. Then it is centrifuged at 5000 rpm for 10 min, transferred to a new tube and stored frozen at −20° C. until further use.

3.2 ELISA Test for Serum Antibody

On the day before experiment, ELISA plates are coated with truncated Marburg virus GP protein (240 aa to 526 aa, prepared by *E. coli* expression) at a concentration of 2 μg/mL, 100 μL/well, and left at 4° C. overnight. On the day of experiment, ELISA plates are washed 3 times with washing solution (PBS+0.2% tween 20) in a plate washer. 120 μL of blocking solution (washing solution+2% BSA) is added to each well, and the mixture is blocked for 1 hour at room temperature. After the plates are washed 3 times in the plate washer, 100 μL of sample dilution buffer (washing solution+0.2% BSA) is added to each well. Serum samples are diluted by a series of 3 times starting at an indicated dilution and incubated at room temperature for 1 hour. 8 serial dilutions are set for each sample and 4 blank control wells without serum are set for each plate. After the plates are washed 5 times, 100 μL of HRP-labeled goat anti-mouse IgG antibody (1:20,000 dilution) is added to each well, and the mixture is incubated for 1 hour at room temperature. After washing 5 times, 100 μL of TMB substrate solution is added to each well, and the reaction is terminated with 2 mol/L sulfuric acid after 6 minutes of color development. Finally, the absorbance at 450 nm is measured using a microplate reader. Taking 2.1 times $OD_{450}$ value of the blank well as the cut-off value, the software GraphPad Prism is used to calculate the antibody titer of each sample. The antibody titer is defined as the reciprocal of the sample dilution corresponding to 2.1 times $OD_{450}$ value of the blank well.

Figure 8:
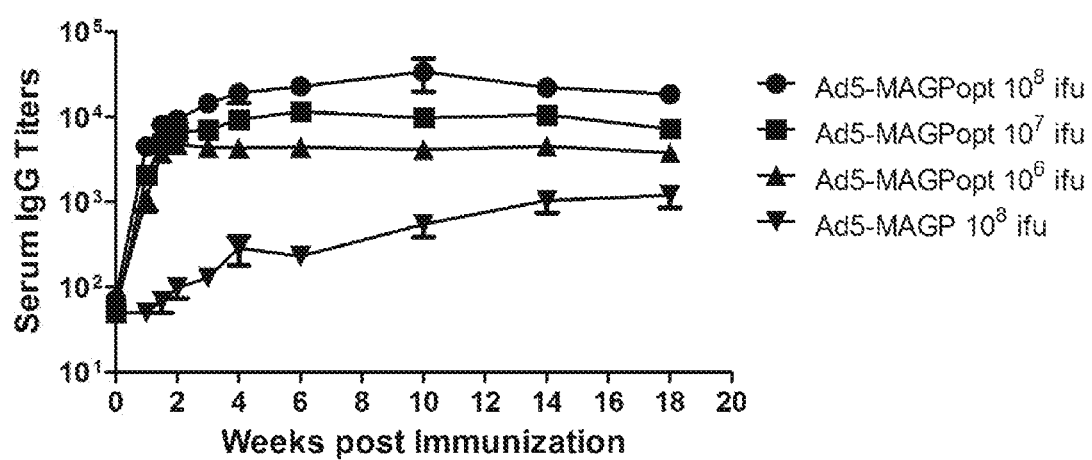
FIG. 8 depicts changes in serum IgG antibody level over time.
Figure 9:
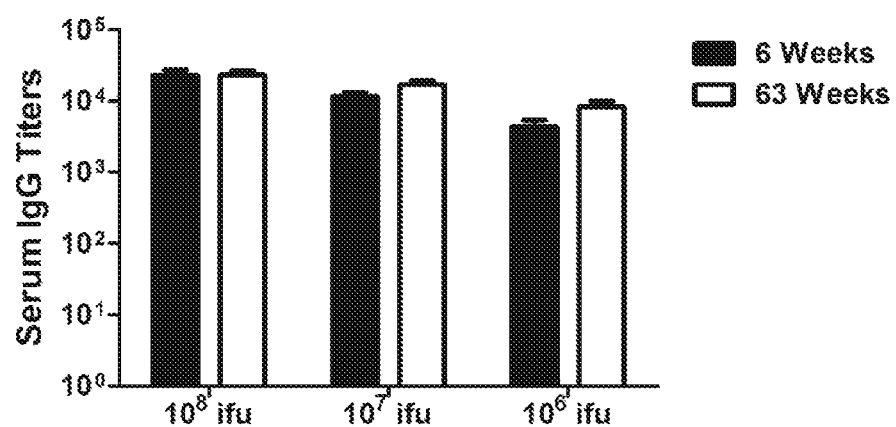
FIG. 9 is the maintenance of serum IgG antibody level.

Antibody data are shown in FIG. 8 and FIG. 9. Codon optimization of MARV GP leads to significant increase in the serum antibody levels induced by Ad5-MAGPopt. High levels of specific antibodies are seen in BALB/c mice immunized with Ad5-MAGPopt within 2 weeks, which last for over 63 weeks in mice. IgG antibody levels of Ad5-MAGPopt in BALB/c mice show a certain dose-dependent relationship.

4. Cellular Immunity.

4.1 Isolation of Splenic Lymphocytes

The mice are sacrificed by cervical dislocation and immersed in 70% alcohol for about 3 min. The spleens are aseptically removed from the mice and placed on the 200-mesh cell sieve in a sterile plate. 10 mL of RPMI1640 complete medium is added, and spleens are gently grinded into single cells with a syringe plunger. 10 mL of RPMI1640 complete medium is added to rinse the cell sieve to obtain more splenocyte. The splenocyte suspension is transferred to a 50 mL centrifuge tube and centrifuged at 500 g for 5 min. The supernatant is discarded, and cells are resuspended in 3 mL of 1× erythrocyte lysis buffer and lysed for 5 minutes at room temperature. 27 mL of RPMI1640 complete medium is added to each tube, and the mixture is centrifuged at 500 g for 5 min. The supernatant is discarded, and cells are washed again with 20 mL of RPMI1640 complete medium. The cells are resuspended with an appropriate volume of medium, filtered through a 200-mesh cell sieve into a 10 mL test tube, counted, and placed on ice until use.

4.2 Flow Cytometry Detection of Specific T Cell Surface Markers and Intracellular Cytokines
4.2.1 In Vitro Stimulation of Mouse Splenocytes The mouse spleen cells is taken for dilution to $4 \times 10^6$ cells/mL, and added to a 24-well plate with 0.5 mL per well. An specific CTL epitope stimulation well and a non-stimulation well are set for each mouse. The specific CTL epitope stimulators are MARV-GP overlapping peptide pool and a MARV-GP CTL epitope LI-9 with a concentration of 2 μg/mL per peptide, the stimulation control is DMSO of the same amount as the peptides. As positive controls, PMA and ionomycin stimulation wells are added, wherein the PMA concentration is 100 ng/mL and the ionomycin concentration is 1 μg/mL. Meanwhile, 1 μL of Brilliant Violet 421™ anti-mouse CD107a is added to each well. The cells are cultured at 37° C. in 5% $CO_2$ incubator for 1 hour, then GolgiStop and/or GolgiPlug is added to each well as the blocker of cytokine secretion. After a total of 6 hours of culture, antigens are stained for flow cytometry detection of intracellular cytokines.

4.2.2 Cell Surface Antigen and Intracellular Cytokine Staining

After in vitro stimulation for 6 hours, spleen cells are transferred to flow tubes and centrifuged at 600 g for 5 minutes at room temperature. The supernatant is discarded. Staining buffer 1 is prepared based on Table 4, with 50 μL per tube, mixed gently, and left at room temperature for 15 minutes in the dark. 3 mL of PBS+2% FBS is added to each tube, and the mixture is centrifuged at 600 g for 5 minutes at room temperature. The supernatant is discarded. Staining buffer 2 is prepared based on Table 4, with 50 μL per tube, mixed gently, and left at room temperature for 20 minutes in the dark. 3 mL of PBS+2% FBS is added to each tube, and the mixture is centrifuged at 600 g for 5 minutes at room temperature. The supernatant is discarded. 200 μL of Cytofix/Cytoperm™ Fixation and Permeabilization Solution is added to each tube, and the mixture is left at room temperature for 20 minutes in the dark to fix and perforate the cells. 1 mL of 1× Perm/Wash™ buffer is added to each tube, and the mixture is centrifuged at 800 g for 5 minutes at room temperature. The supernatant is discarded. Staining buffer 3 is prepared based on Table 4, with 50 μL per tube, mixed gently, and left at room temperature for 30 minutes in the dark. 2 mL of 1× Perm/Wash™ buffer is added to each tube, and the mixture is centrifuged at 800 g for 5 minutes at room temperature. The supernatant is discarded. 3 mL of PBS is added to each tube, and the mixture is centrifuged at 800 g for 5 minutes at room temperature. The supernatant is discarded. Cells in each tube are resuspend with 150 μL PBS, and left at 4° C. in the dark, until further test.

TABLE 4

Table of flow cytometry staining buffer preparation (unit, μL)

| Component | Volume (per preparation) |
|---|---|
| PBS (staining buffer 1) | 50.0 |
| LIVE/DEAD ™ Fixable Near-IR Dead Cell Stain Buffer | 0.25 μL/mL |
| Mouse BD Fc Block ™ | 1.0 |
| PBS + 2% FBS (staining buffer 2) | 50.0 |
| APC/Cy7 anti-mouse CD14 | 0.25 |
| APC/Cy7 anti-mouse CD19 | 0.15 |
| Alexa Fluor ® 700 anti-mouse CD4 | 0.15 |
| 1 × Perm/Wash ™ Buffer (staining buffer 3) | 50.0 |
| PerCP/Cy5.5 anti-mouse CD3 | 0.20 |
| FITC anti-mouse CD8a | 0.10 |
| PE anti-mouse IFNγ | 0.25 |
| PE/Cy7 anti-mouse TNF | 0.50 |
| Brilliant Violet 605 ™ anti-mouse IL-2 | 0.50 |
| Brilliant Violet 510 ™ anti-mouse CD154 | 0.50 |

4.2.3 Test on the Machine

BD FACS Canto™ is used for flow cytometry. Firstly, the voltage of each channel is regulated to the appropriate level, and single-fluorescent stained samples are used to adjust the fluorescence compensation between dyes. Then, samples are loaded in order and data are collected. Single cells are gated by FSC-A and FSC-H, lymphocytes are gated by FSC and SSC, living CD3 cells are gated by PerCP/Cy5.5 and APC/Cy7, and CD8$^+$ T cells and CD4$^+$ T cells are gated by FITC and Alexa Fluor® 700. Finally, the PE channel, PE/Cy7 channel, Brilliant Violet 605 channel, Brilliant Violet 421 and Brilliant Violet 510 channels are used to count the percentage of IFNγ, TNF, IL-2, CD107a and CD154 positive cells in CD8$^+$ T cells and CD4$^+$ T cells, respectively.

4.2.4 Intracellular Cytokine Staining

Figure 10:
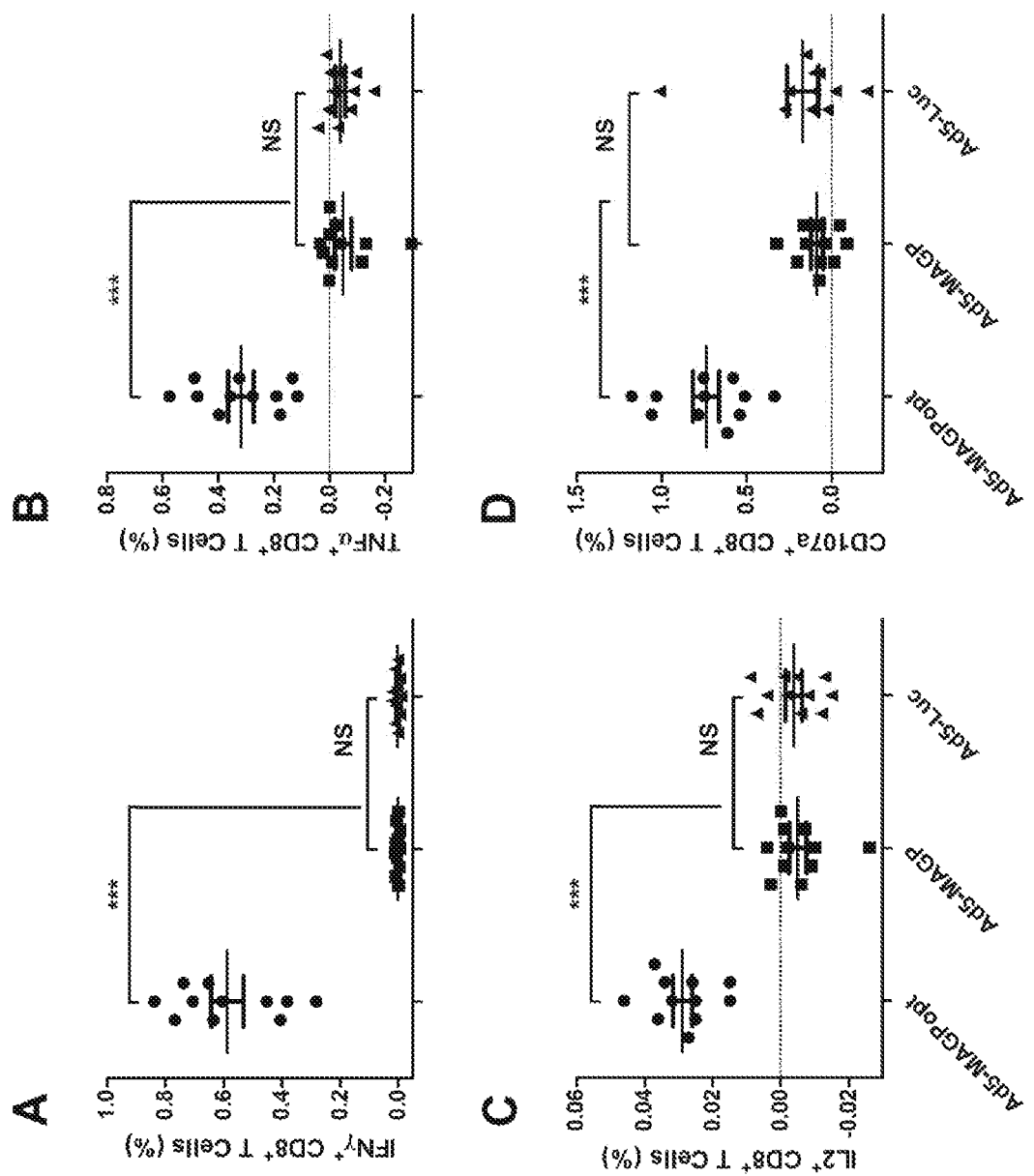
FIG. 10 shows the statistical analysis of the results of flow cytometry with intracellular cytokine staining.
Figure 11:
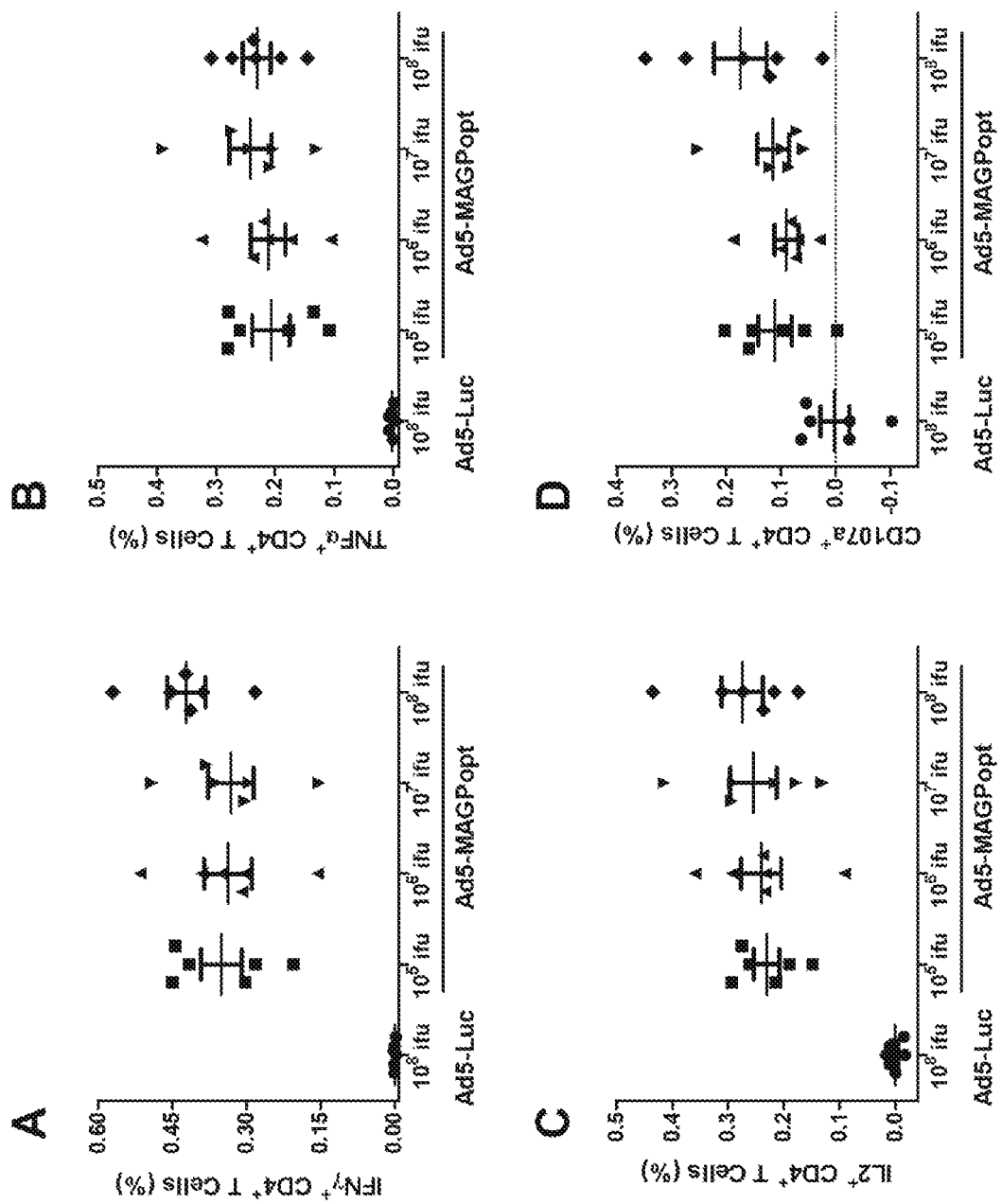
FIG. 11 provides CD4$^+$ T cell immune response induced by different doses of Ad5-MAGPopt.
Figure 12:
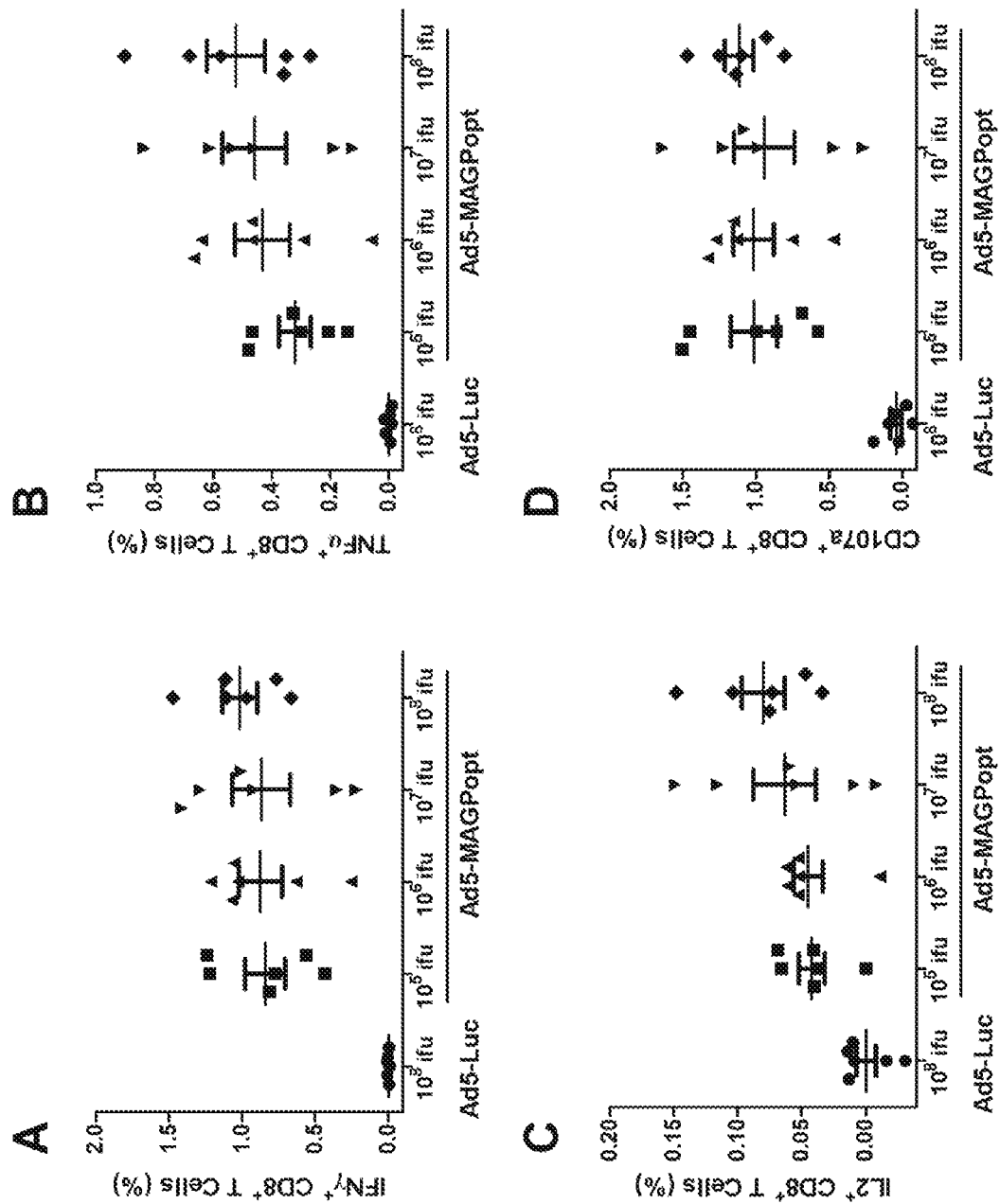
FIG. 12 is a graph of CD8$^+$ T cell immune response induced by different doses of Ad5-MAGPopt.
Figure 13:
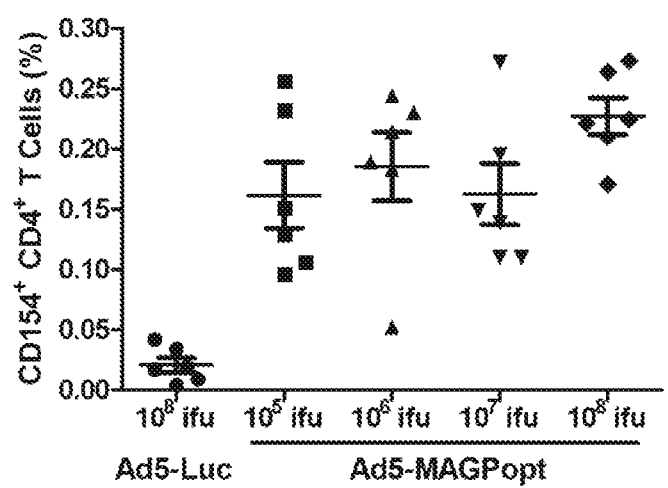
FIG. 13 depicts CD154$^+$CD4$^+$ T cell response induced by different doses of Ad5-MAGPopt.

The intracellular cytokine staining show that after splenocytes from Ad5-MAGPopt-immunized mice are stimulated by MARV-GP overlapping peptide pool and MARV-GP CTL epitope LI-9, CD8$^+$ T cells and CD4$^+$ T cells can secrete a large amount of IFN-γ, TNF-α, and IL-2 cytokines, with remarkably higher expression of cytotoxicity marker CD107a, which is significantly higher than that of the immunization with non-codon-optimized Ad5-MAGP group and the control Ad5-Luc group (see FIG. 10, NS, P>0.05; ***, P<0.001). Meanwhile, remarkably higher expression of CD154 on CD4$^+$ T cells is detected in spleen cells from Ad5-MAGPopt-immunized mice (see FIG. 13), suggesting that specific T cells induced by Ad5-MAGPopt can activate B cells. Cellular immune response of mice immunized with Ad5-MAGPopt at different dose indicate that the difference of cellular immune response (IFN-γ, TNF-α, IL-2, and CD107a) of CD8$^+$ T cells and CD4$^+$ T cells induced by Ad5-MAGPopt at 1×10$^8$ ifu, 1×10$^7$ ifu, 1×10$^6$ ifu or 1×10$^5$ ifu between BALB/c mice immunized with the above dose is not significantly different via analysis of variance (see FIG. 11 and FIG. 12).

4.3. ELISPOT Assay of Cytokines

BD™ ELISPOT mouse IFN-γ Set is used for ELISPOT assay of IFN-γ. The procedure is conducted according to the kit instructions. ELISPOT plate is coated with 5 μg/mL anti-mouse IFN-γ antibody and left at 4° C. overnight. RPMI 1640+10% FBS medium is used to block the plate at room temperature for 2 hour. Discard the blocking solution, 50 μL of RPMI1640+10% FBS medium containing MARV-GP overlapping peptide pool and MARV-GP CTL epitope LI-9 (concentration, 2 μg/mL per peptide) or non-stimulation control medium containing the same volume of DMSO is added to each well in advance according to the layout of the plate. 50 μL of isolated spleen cells (4×10$^6$ cells/mL) are added to the specific wells, with two wells of peptide stimulation and two wells without stimulation for each mouse. Cells are cultured at 37° C. in 5% $CO_2$ incubator for 12-24 hours. The following day, cells in the plate are discarded, the plates are washed twice with 200 μL distilled water, and then washed 3 times with washing solution (PBS+0.05% tween-20), left for 2-3 minutes each time. Discard the washing solution, added 100 μL biotinylated anti-mouse IFNγ (diluted at 1:250 in PBS+10% FBS) in each well, and incubate at room temperature for 2 hours. The plates are washed 3 times with washing solution, left for 2-3 minutes each time. Add 100 μL streptavidin-horseradish peroxidase (diluted at 1:100 in PBS+10% FBS) in each well, and incubate at room temperature for 1 hour. Wash the plates for 4 times with washing solution, and 3 times with PBS. Develop the spots with BD™ ELISPOT AEC substrate set. When the spots in the wells grow to a suitable size (usually reaction at room temperature for 15-25 minutes), discard the substrate solution, and terminate the reaction by washing extensively in deionized water. After the plate is dried, count the spots with an enzyme-linked spot imaging analysis system.

Figure 14:
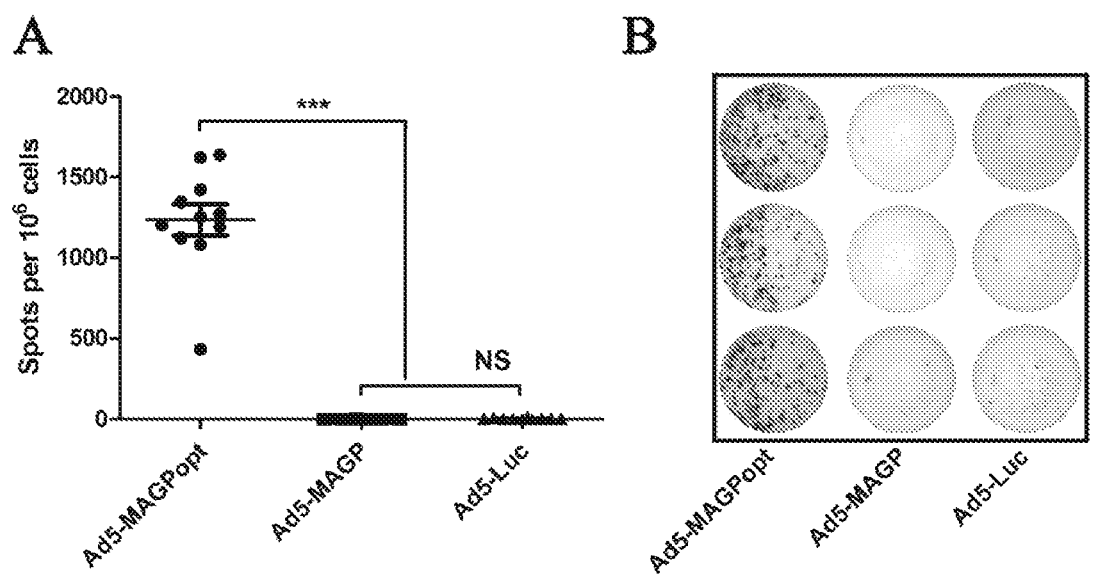
FIG. 14 is the statistical analysis and representative results of ELISPOT detection of IFN-$\gamma$ secretion.
Figure 15:
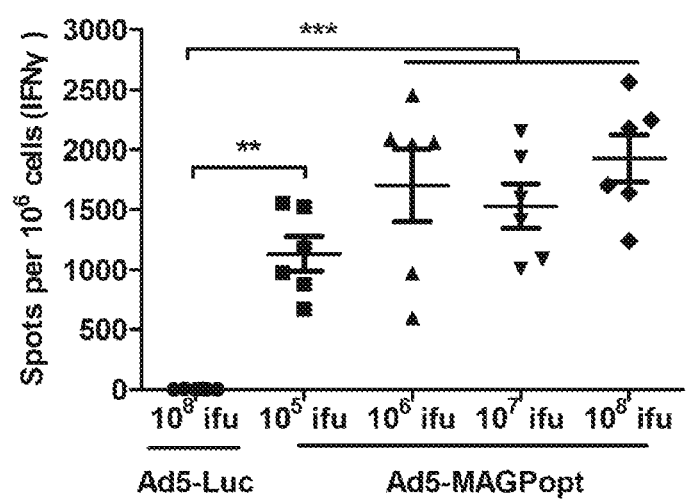
FIG. 15 shows IFN-$\gamma$ secretion induced by different doses of Ad5-MAGPopt.

Similar to the intracellular cytokine test by flow cytometry, after splenocytes from Ad5-MAGPopt immunized mice are stimulated by Marburg GP overlapping peptide pool and Marburg GP CTL epitope LI-9, a large amount of specific IFN-γ spots appear, which is significantly higher than that of Ad5-MAGP group and the Ad5-Luc control group (see FIG. 14, NS, P>0.05; , P<0.01; *, P<0.001). Meanwhile, specific IFNγ spots induced by different doses (1×10$^8$ ifu, 1×10$^7$ ifu, 1×10$^6$ ifu and 1×10$^5$ ifu) of Ad5-MAGPopt in immunized BALB/c mice show no dose-dependence effect via analysis of variance (see FIG. 15).

5. Summary of Immunological Evaluation

Intramuscular injection of MARV-GP codon-optimized Marburg virus disease vaccine Ad5-MAGPopt induces strong humoral and cellular immune responses in the immunized BALB/c mice.

Example 3. Evaluation on the Protective Efficacy of Ad5-MAGPopt on Mouse Models

SPF BALB/c mice (4-6 weeks old) are divided into 4 groups (see Table 5), and intramuscularly injected with Ad5-MAGPopt (rename as Ad5-MARY) at 10$^8$ ifu, 10$^7$ ifu or 10$^6$ ifu, or PBS of equal volume. Four weeks after immunization, mice are transferred to the biosafety level 4 laboratory for MA-MARV (Marburg virus mouse adaptive strains) challenge by intraperitoneal injection and the challenge dose is 2000×LD$_{50}$. The survival and weight changes of the mice are recorded within 14 days after challenge, and the survival are recorded for an additional 14 days.

TABLE 5

Groups of study on the protective efficacy of Ad5-MAGPopt

| Name | Dose | Route of immunization | Number of mice in the group |
| --- | --- | --- | --- |
| Ad5-MARV | 10$^8$ ifu | Intramuscularly | 10 |
| Ad5-MARV | 10$^7$ ifu | Intramuscularly | 10 |
| Ad5-MARV | 10$^6$ ifu | Intramuscularly | 10 |
| PBS | 0 ifu | Intramuscularly | 10 |

Figure 16:
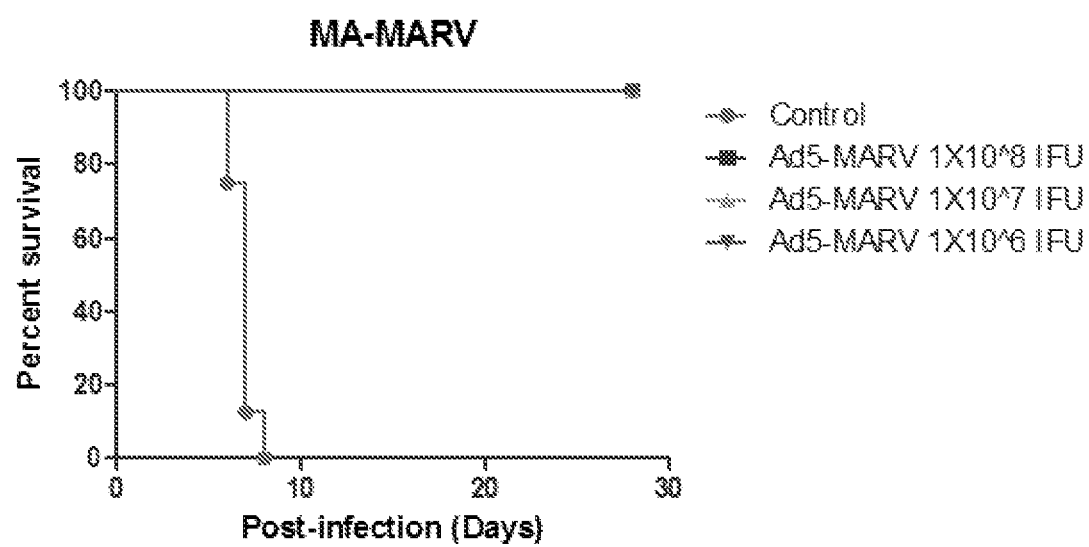
FIG. 16 provides the protective effect of Marburg virus disease vaccine on mouse model.
Figure 17:
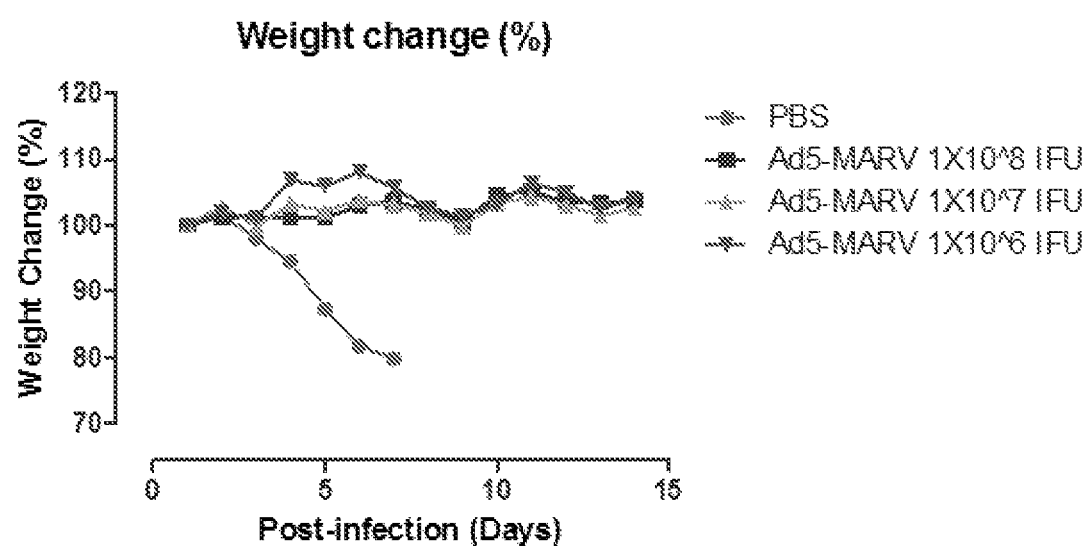
FIG. 17 is a graph of the change of body weight of mice after challenge.

28 days after immunization, MA-MARV challenge is conducted in mice immunized with Ad5-MARV at different dose levels or control mice. All mice immunized with the Ad5-MARV (10$^8$ ifu/mouse, 10$^7$ ifu/mouse, and 10$^6$ ifu/mouse) survive, but all mice in PBS control group die within 6 to 8 days after challenge (see FIG. 16). None of Ad5-MARV-immunized mice experience weight loss within 14 days after challenge, but those in the PBS control group begin to lose weight on day 3 after challenge until death (see FIG. 17).

INDUSTRIAL APPLICABILITY

The present invention discloses a Marburg virus disease vaccine with human replication-deficient adenovirus as vector, a preparation method and a use in the preparation of vaccine agents. The Marburg virus disease vaccine provided by the present invention is easy for industrial production, with industrial applicability.

The invention claimed is:

1. An isolated nucleic acid molecule encoding a Marburg virus envelope glycoprotein, wherein the isolated nucleic acid molecule comprises a nucleic acid sequence shown in SEQ ID NO: 1.

2. A vector containing the nucleic acid molecule of claim 1.

3. The vector of claim 2, wherein the vector is pDC316.

4. A human replication-deficient recombinant adenovirus comprising the nucleic acid molecule of claim 1.

5. A method of inducing an immune response in a subject against Marburg virus, comprising administering to the subject a composition comprising the recombinant adenovirus of claim 4.

6. The method of claim 5, wherein the composition is administered to the subject by an injection.

7. A method of preparation of the human replication-deficient recombinant adenovirus of claim 4, comprising:

(1) constructing a shuttle plasmid vector containing an isolated nucleic acid molecule encoding a Marburg virus envelope glycoprotein;
(2) transfecting the vector of step (1) into host cells together with backbone plasmids;
(3) cultivating the host cells of step (2); and
(4) harvesting human replication-deficient recombinant adenoviruses released from the cells of step (3).

8. The method of claim 7, wherein the vector of step (1) is pDC316.

9. The method of claim 7, wherein the backbone plasmid of step (2) is pBHGloxΔE1, 3Cre.

10. The method of claim 7, wherein the host cells of step (3) are HEK293 cells.

11. The method of claim 7, wherein the recombinant adenoviruses of step (4) are extracted and purified through a two-step column chromatography with source 30Q and sepharose 4ff.

* * * * *

UNITED STATES PATENT AND TRADEMARK OFFICE
CERTIFICATE OF CORRECTION

| | | |
|---|---|---|
| PATENT NO. | : 11,453,704 B2 | Page 1 of 1 |
| APPLICATION NO. | : 16/756610 | |
| DATED | : September 27, 2022 | |
| INVENTOR(S) | : Wei Chen et al. | |

It is certified that error appears in the above-identified patent and that said Letters Patent is hereby corrected as shown below:

In the Specification

Column 3, Lines 51-52 should read: "infection."

Column 5, Line 66 should read: "washed 4 times with Western blot wash buffer."

Column 8, Lines 31-32 should read: "equilibrate the column 0%-30% solution B is used for gradient elution at 10 mL/min for 50 min, and the elution peaks"

Column 8, Lines 43-44 should read: "Popt and Ad5-MAGP"

Column 8, Line 44 should read: "3.4.1 PCR Amplification of MARV-GP Sequence and Sequencing"

Column 11, Lines 59-60 should read: "Markers and Intracellular Cytokines"

Column 11, Line 60 should read: "4.2.1 In Vitro Stimulation of Mouse Splenocytes"

Column 12, Line 64 should read: "4.2.3. Test on Flow Cytometry"

Signed and Sealed this
Fifteenth Day of November, 2022

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 2088
<212> TYPE: DNA
<213> ORGANISM: Marburg virus

<400> SEQUENCE: 1

| | | | | | | |
|---|---|---|---|---|---|---|
| ccaagcttgc | cgccaccatg | gacgccatga | agcggggcct | ctgctgtgtt | ctgctgctct | 60 |
| gcggcgccgt | gttcgtgagt | aactcgttac | ccattctgga | gattgccagc | aacatccagc | 120 |
| cccagaacgt | ggattccgtg | tgctccggca | ccctgcagaa | gaccgaagat | gtccatctca | 180 |
| tgggcttcac | cctgtccggg | cagaaggtcg | ccgactcgcc | cctggaggcc | agcaagcgct | 240 |
| gggccttccg | cgcaggcgtc | cctcctaaga | acgtggaata | cacggaggga | gaggaggcca | 300 |
| agacttgtta | caacatctca | gtaaccgacc | cctccggtaa | aagtctcctg | ctcgaccctc | 360 |
| cgacgaacat | ccgcgactac | cccaagtgca | agacaatcca | ccacattcag | ggccagaatc | 420 |
| cgcacgccca | gggtatcgcc | ctgcacctgt | ggggcgcttt | tttcctgtac | gaccgaatcg | 480 |
| cctccaccac | catgtaccgg | gggaaggttt | ttaccgaggg | caatatcgcc | gccatgattg | 540 |
| tgaataagac | cgtccacaag | atgatcttct | ccaggcaggg | gcagggatac | cggcacatga | 600 |
| acctgacctc | cactaacaag | tactggacta | gttccaacgg | tacccagacc | aacgacactg | 660 |
| gctgctttgg | gaccctccag | gagtacaact | ccaccaaaaa | ccagacttgt | gccccgtcca | 720 |
| aaaagccccct | gccctgcct | accgccacc | cggaagtgaa | gctgacatct | acatcgaccg | 780 |
| acgcaacaaa | actcaatact | accgacccca | atagtgacga | cgaggacctg | accaccagtg | 840 |
| gcagcggctc | cggcgagcag | gagccataca | ccacctcgga | cgcagcaacc | aagcagggcc | 900 |
| tgtcgtccac | gatgccgcct | accccgtcgc | cccagccctc | gaccccgcag | cagggcggca | 960 |
| ataataccaa | ccattctcag | ggggtcgtta | ccgagcccgg | caagaccaac | acgactgctc | 1020 |
| agccatccat | gccaccccac | aacaccacca | ctatctcgac | caacaacact | tcaaagcaca | 1080 |
| acctctcgac | ccccagtgtc | ccaatccaga | acgccaccaa | ctataacacg | cagtccacag | 1140 |
| cgcccgagaa | cgagcagaca | agtgcccct | ctaagacgac | cctcctcccc | accgagaacc | 1200 |
| ccacaaccgc | caagtccacc | aactcaacca | agtcccccac | gacgaccgtt | ccaacacca | 1260 |
| ccaacaagta | ctcaacctct | ccttcgccta | ccccaaactc | caccgcgcag | caccttgtgt | 1320 |
| acttccgccg | gaagcgaaac | atcctgtggc | gcgagggaga | catgttccct | ttcctcgatg | 1380 |
| gactgatcaa | cgcccccatc | gactttgatc | cagtccccaa | caccaagacg | atcttcgatg | 1440 |
| aaagtagtag | ttcgggggct | agtgcagaag | aggaccagca | tgcgagtcct | aacatctccc | 1500 |
| tgaccctctc | ctacttcccc | aaggtgaacg | agaataccgc | ccactccggc | gagaatgaga | 1560 |
| acgattgcga | tgccgaactg | aggatctgga | gtgtgcagga | ggacgacctg | gcggctggcc | 1620 |
| tgtcttggat | ccccttcttt | gggccgggca | tcgagggcct | gtacaccgcc | ggcctgatta | 1680 |
| aaaaccagaa | caacctggtt | tgccgcctga | gaagactggc | aaaccagact | gccaagtccc | 1740 |
| tggaactgct | cttacgcgtc | accaccgagg | agcggacctt | ttcgctcatc | aaccgccacg | 1800 |
| ccatcgactt | cctgctggcc | cggtgggggcg | gtacgtgcaa | agtgctgggc | cccgactgct | 1860 |
| gcatcggcat | cgaggatctc | agccgcaaca | tctctgagca | aatcgatcag | atcaagaagg | 1920 |
| atgagcagaa | ggaaggtacc | ggctggggcc | tggggggaa | gtggtggacc | agtgactggg | 1980 |
| gcgtgctgac | taacctgggc | atcctgctgc | tgctatcgat | cgccgtgctc | atcgccctgt | 2040 |
| cttgcatctg | ccgtatcttc | accaaatata | tcggctaagt | cgacgtct | | 2088 |

<210> SEQ ID NO 2
<211> LENGTH: 2073
<212> TYPE: DNA
<213> ORGANISM: Marburg virus

<400> SEQUENCE: 2

```
ccaagcttgc cgccaccatg aaaaccacat gtctccttat cagtcttatc ttaatccaag      60
gggtaaaaac tctccctatt ttagagatag ccagtaacat tcaaccccaa aatgtggatt     120
cagtatgctc cgggactctc cagaagacag aagacgttca tctgatggga ttcacactga     180
gcgggcaaaa agttgctgat tcccctttag aggcatccaa acgatgggcc ttcagggcag     240
gtgtacctcc caagaatgtt gagtatacag aaggggagga agctaaaaca tgttacaata     300
taagtgtaac ggatccctct ggaaaatcct tgctgttaga tcctcctacc aacatccgtg     360
actatcctaa atgcaaaact atccatcata ttcaaggtca aaaccctcat gcacagggga     420
tcgctctcca tttgtgggga gcatttttct tgtatgatcg catcgcctcc acaacgatgt     480
atcgaggcaa agtcttcact gaagggaaca tagcagctat gattgtcaat aagacagtgc     540
acaaaatgat tttctcgagg caaggacaag ggtaccgtca catgaaccta acttctacta     600
ataaatattg gacaagtagc aacggaacgc aaacgaatga cactggatgc ttcggtactc     660
ttcaagaata taattctaca agaaccaaa catgtgctcc gtccaaaaaa cctttaccac     720
tgcccacagc ccatccggag gtcaagctca ctagcacctc aactgatgcc accaaactca     780
ataccacaga cccaaacagt gatgatgagg acctcacaac atctggctca gggtctggag     840
aacaggaacc ttacacaact tctgacgcag ccacgaagca agggctttca tcaacaatgc     900
cgcccactcc ctcaccacaa ccaagcacgc cacagcaagg aggaaacaac acgaaccatt     960
cccaaggtgt tgtgactgaa cccggcaaaa ccaacacaac tgcacaaccg tccatgcccc    1020
ctcacaacac tactacaatc tctactaaca cacctccaa gcacaacctc agcactccct    1080
ctgtaccaat acaaaatgcc actaattaca acacacagag cacggcccct gaaaatgagc    1140
aaaccagtgc cccctcgaaa acaaccctgc ttccaacaga aaatcctaca acagcaaaga    1200
gcaccaatag tacaaaaagc cccactacaa cagtaccaaa tacgacaaat aagtattcca    1260
ccagtccctc cccacccccc aactcgactg cacaacatct tgtatatttc agaaggaaac    1320
gaaatattct ctggagggaa ggcgacatgt tcccttttct ggatgggtta ataaatgctc    1380
cgattgattt tgatccggtt ccaaatacaa agacaatctt tgatgaatcc tctagttctg    1440
gtgcttcagc tgaggaagat cagcatgcct ccctaatat cagtttaact ttatcttact    1500
ttcctaaggt aaatgaaaac actgcccact ctggagaaaa tgaaaatgat tgtgatgcag    1560
agttaagaat ttggagtgtt caggaggacg acctggcagc aggactcagt tggataccgt    1620
ttttttggccc tggaatcgaa ggactttata ctgctggttt aattaaaaat caaataatt    1680
tggtttgcag gttgaggcgt ctagccaatc agactgccaa atccttggaa ctcttattaa    1740
gagtcacaac cgaggaaaga acattttcct taatcaatag acatgccatt gatttttac    1800
tcgcaaggtg gggaggaaca tgcaaagtgc ttggacctga ttgttgcatc ggaatagaag    1860
acttgtccag aaatatttca gaacaaattg atcaaatcaa aaaggacgaa caaaagagg    1920
ggactggttg gggtctgggt ggtaaatggt ggacatcaga ctggggtgtt cttactaact    1980
tgggcatctt gctactactg tccatagctg tcttaattgc tctgtcctgt atttgtcgta    2040
tttttactaa atatattgga taagtcgacg tct                                  2073
```